(12) United States Patent
Madic et al.

(10) Patent No.: US 7,015,340 B2
(45) Date of Patent: Mar. 21, 2006

(54) HEAT-SENSITIVE COMPOUNDS EXHIBITNG A CLOUD POINT WHICH CAN BE USED AS EXTRACTANTS FOR THE SEPARATION OF METALS IN AQUEOUS SOLUTION

(75) Inventors: Charles Madic, Thiais (FR); Laurence Berthon, Connaux (FR); Nicole Zorz, Bagnols/Ceze (FR); Hélène Coulombeau, Orsay (FR); Fabienne Testard, Paris (FR); Thomas Zemb, Viroflay (FR); Sébastien Gibanel, La Force (FR); Chantal Larpent, Versailles (FR); Krystyna Baczko, Orsay (FR)

(73) Assignee: Commissariat a L'Energie Atomique, Paris (FR)

( * ) Notice: Subject to any disclaimer, the term of this patent is extended or adjusted under 35 U.S.C. 154(b) by 0 days.

(21) Appl. No.: 10/488,621

(22) PCT Filed: Sep. 6, 2002

(86) PCT No.: PCT/FR02/03038

§ 371 (c)(1),
(2), (4) Date: Mar. 2, 2004

(87) PCT Pub. No.: WO03/022798

PCT Pub. Date: Mar. 20, 2003

(65) Prior Publication Data

US 2004/0242769 A1    Dec. 2, 2004

(51) Int. Cl.
*C07C 235/12* (2006.01)
*C22B 60/02* (2006.01)
(52) U.S. Cl. .................. 554/56; 530/300; 530/350; 554/64; 525/54.1
(58) Field of Classification Search ............... 525/54.1; 530/300, 350; 554/56, 64
See application file for complete search history.

(56) References Cited

U.S. PATENT DOCUMENTS 4,154,674 A    5/1979    Warshawsky et al.

FOREIGN PATENT DOCUMENTS

WO    WO 00/73521 A1    12/2000

OTHER PUBLICATIONS

Bergbreiter, David E. et al, *Sequestration of Trace Metals Using Water-Soluble and Fluorous Phase-Soluble Polymers*, Angewandte Chemie. International Edition, 2000, pp. 1039-1042, vol. 39, No. 6, Weinheim, Germany.
Grillo, Isabelle, *Thesis of the University Paris XI*, 1998, p. 175, p. 25, II 16-20.

Hinze, Willie L. et al, *A Critical Review of Surfactant-Mediated Phase Separations (Cloud-Point Extractions): Theory and Applications*, Critical Reviews in Analytical Chemistry, 1993, pp. 133-177, 24 (2), CRC Press, Inc.
Huibers, Paul D. T. et al, *Predicting Surfactant Cloud Point from Molecular Structure*, Journal of Colloid and Interface Science, 1997, pp. 132-136, 193, Article No. CS975053, Academic Press.
Kocienski, Philip J., *Protecting Groups*, 1994, pp. 83-87, Georg Thieme Verlag Stuttgart, New York.
Philippon, Annie et al, *Macrocyclic Ethers By Free Radical Cyclizations*, Synthetic Communications, 1997, pp. 2651-2682, 27 (15), Marcel Dekker, Inc.
Popovitz-Biro, R. et al, *A New Series of Amphiphilic Molecules Forming Stable Z-Type (Polar) Langmuir-Blodgett Films*, J. Amer. Chem. Soc., 1990, pp. 2498-2506, vol. 112, No. 7, American Chemical Society.
Schott, Hans et al, *Effect of Inorganic Additives on Solutions of Nonionic Surfactants II*, Journal of Pharmaceutical Sciences, Apr. 1975, pp. 658-664, vol. 64, No. 4.
Takeshita, Kenji et al, *Extraction of lanthanide elements by thermosensitive polymer gel copolymerized with acidic phosphorous compound*, Solvent Extraction and Ion Exchange, 2000, pp. 375-386, 18 (2), Marcel Dekker, Inc.
Tani, Hirofumi et al, *Micelle-mediated extraction*, Journal of Chromatography A, 1997, pp. 229-241, 780, Elsevier Science.
Wassermann, Hubert et al, *Symmetric Di- or Tetra-alkyl Substituted Monodisperse Polyoxyethyleneglycols: Synthesis and Surface Properties*, J. Chem. Soc. Perkin Trans. 2, 1992, pp. 2043-2047.

*Primary Examiner*—Irina S. Zemel
(74) *Attorney, Agent, or Firm*—Hutchison & Mason PLLC (57) ABSTRACT

The invention relates to a heat-sensitive compound having the property of being soluble in water below a critical temperature $T_c$ and insoluble in water above this temperature $T_c$, this property being thermally reversible, characterized in that it comprises a first amphiphilic and thermally reversible part corresponding to one of the following formulae (I) and (II):

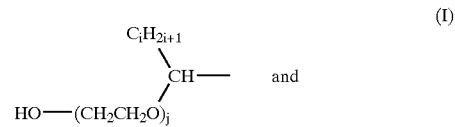

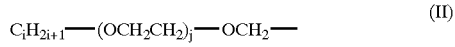

in which i is an integer ranging from 1 to 20 and j is an integer ranging from 3 to 30.

This compound can be used to extract a chemical entity, such as uranium.

25 Claims, 1 Drawing Sheet

Figure 1

HEAT-SENSITIVE COMPOUNDS EXHIBITNG A CLOUD POINT WHICH CAN BE USED AS EXTRACTANTS FOR THE SEPARATION OF METALS IN AQUEOUS SOLUTION

TECHNICAL FIELD

The invention relates to a heat-sensitive compound exhibiting a cloud point, that is to say having the property of being soluble in water below a critical temperature $T_c$ (also known as cloud point) and insoluble in water above this temperature $T_c$, this property being thermally reversible.

Such compounds can be used in particular as extractants for the separation of chemical entities, in particular metals, such as actinides and lanthanides, or of any other nonmetallic element, by the action of an external stimulus which is a temperature variation.

The chemical entity can in particular be in the form of simple ions (1 single atom) or of complex ions composed of a group of atoms.

STATE OF THE PRIOR ART

The use of heat-sensitive compounds for the separation of metals has already been envisaged, as is described by Bergbreiter D. E., Koshti N., Franchina J. G., Frels J. G., Angew. Chem. Int. Ed., 39, 2000, 1040–2 [11], and by Takeshita K. and Nakano Y., Solvent Extraction and Ion Exchange, 18(2), 2000, 375–86 [2].

In the reference [1], use is made, as heat-sensitive compound, of a copolymer of N-isopropylacrylamide and of N-acryloyloxysuccinimide (PNIPAM-c-NASI) bonded to hydroxamic acid, which exhibits a critical temperature of 31° C. This heat-sensitive compound can be used to separate Fe(III) ions. In this case, it is added to the aqueous solution comprising the Fe(III) ions, which results in a homogeneous solution with the red colour characteristic of the ferric complex. When the temperature is increased above 31° C., precipitation of the coloured polymer is obtained, leaving a colourless supernatant. Quantitative determination of the ferric ions in the supernatant shows that more than 99% of the ferric ions have been sequestered in the precipitated polymer, i.e. a sequestration capacity of the polymer of the order of 2 mg of Fe(III) per gram of polymer in the example given.

In the reference [2], use is made of a heat-sensitive compound composed of a gel of copolymer of N-isopropylacrylamide (NIPA) and of 2-methacryloyloxyethyl-phosphate acid for extracting lanthanides from an aqueous solution comprising nitrate ions. In aqueous solution, these copolymers form gels which dehydrate and shrink in a gradual fashion as the temperature increases, thus trapping the ion to be separated. Typically, the experiments were carried out on 50 ml of aqueous solution comprising 500 ppm of La(III) or of Sm(III) and 50 mg of heat-sensitive compound, i.e. an ion/polymer ratio by weight of 1/2.

In the reference [1], use may also be made of a PNIPAM-c-NASI copolymer bonded to 3-hydroxy-2-pyridinone in order to separate Fe(III) and Cu(II) using the same principle.

Processes for extraction by means of micellar solutions of nonionic surfactants exhibiting a cloud point are also known, these processes being used mainly in analytical chemistry for the extraction of organic compounds, of proteins or other biomolecules, and of metal cations, as is described by Hinze W. L., Pramauro E., Critical Reviews in Analytical Chemistry, 24(2), 1993, 133–77 [3], and by Tani H., Kamidate T., Watanabe H., J. Chromatogr. A., 780, 1997, 229–241 [4].

The principle of these extractions is based on:
(1) the dissolution of the solute to be extracted in the micelles of surfactants in aqueous solution at a temperature below the cloud point $T_c$, and
(2) the phase separation, i.e. demixing, induced by increasing the temperature above $T_c$: the solute, dissolved in the micelles, is entrained with the surfactant in the concentrated phase.

One of the major advantages of this technique is the concentrating. The effectiveness of the extraction depends on the affinity of the solute for the micelles of surfactants (micelles/aqueous phase partition coefficient): it is much higher for hydrophobic solutes than for hydrophilic polar solutes. The extraction of metal ions, which have little affinity with common surfactants, can be carried out by introducing, into the system, an organic chelating agent which has the role of complexing the metal ion and of making possible its dissolution in the micelles in the form of a more hydrophobic metal chelate and then its subsequent separation when the temperature is increased. The effectiveness of the separation depends on the hydrophobicity of the chelating agent and of the complex.

In the majority of cases, the studies were carried out with the objective of analysing trace amounts, extraction by cloud point being used as preconcentrating stage.

The studies described relate to the separation of transition metal cations Ni(II), Zn(II), Cu(II) or Co(II) and of the uranyl cation U(VI) in low concentrations.

The surfactants used are generally polyethoxylated alkylphenols (Triton X114, X100, PONPE, the $T_c$ values of which are respectively of the order of 25, 65 and 5° C.) at concentrations of the order of 0.1 to 0.5% by weight, much greater than their critical micelle concentration. The ratios of molar concentration of surfactant with respect to the cation are very high: of the order of 50 to 1000.

The chelating agents used are complexing agents well known for these ions, such as, for example, 1-(2-pyridylazo)-2-naphthol (PAN), for the separation of Zn(II) or U(VI), or 2-(2-thiazoloylazo)-4-phenol derivatives variously substituted on the phenol, such as TAC ($CH_3$), TAMP ($OCH_3$), TAEP ($OC_2H_5$) and TAPP ($C_6H_5$), for the separation of Ni(II), Zn(II), Fe(II) or Cd(II).

Furthermore, provision has been made, in U.S. Pat. No. 4,154,674 [12], to use, for selectively extracting metal cations from a solution, polyoxyalkylene glycol derivatives and in particular derivatives in which the polyoxyalkylene chain is bonded to a polymer of the polystyrene type or a copolymer of styrene and of another monomer, such as divinylbenzene.

Provision has also been made, in WO-A-00/73521 [13], to separate the lanthanides from the actinides present in an aqueous medium by nanofiltration/complexing, using ligands of poly(amino acid) type.

DESCRIPTION OF THE INVENTION

A subject-matter of the present invention is specifically novel heat-sensitive compounds which can be used as extractants for various chemical entities, for example for metals, such as actinides and lanthanides, in the form of simple or complex metal ions, and for any other nonmetallic chemical entity, by employing a stage of complexing the chemical entity by the heat-sensitive compound, at a temperature below the critical temperature $T_c$ of this compound, and then a second stage of separating the complex formed, chemical entity/heat-sensitive compound, by increasing the temperature to a temperature greater than $T_c$.

According to the invention, the heat-sensitive compound has the property of being soluble in water below a critical temperature $T_c$ and insoluble in water above this temperature $T_c$, this property being thermally reversible. The compound comprises a first amphiphilic and thermally reversible part which is derived from a polyethoxylated nonionic surfactant and which corresponds to one of the following formulae (I) and (II):

$$\begin{array}{c} C_iH_{2i+1} \\ \diagdown \\ CH- \\ \diagup \\ HO-(CH_2CH_2O)_j \end{array} \quad \text{and} \quad (I)$$

$$C_iH_{2i+1}-(OCH_2CH_2)_j-OCH_2- \quad (II)$$

in which i is an integer ranging from 1 to 20 and j is an integer ranging from 3 to 30, this first part being bonded chemically to a second part capable of complexing a chemical entity.

Thus, the first part of the heat-sensitive compound according to the invention is derived from a polyethoxylated nonionic surfactant of formula $R-O(CH_2CH_2O)_n-H$ in which R represents a linear or branched alkyl chain and n is an integer ranging from 3 to 30.

Surfactants of this type are described, for example, in Huibers P. D. T., Shah D. O., Katrizky A. R., J. Colloid and Interface Sci., 193, 1997, 132–6 [51]. They exhibit a cloud point which can lie within a wide range from 6 to 100° C.

This cloud point, which will determine the critical temperature of the heat-sensitive compound, depends on the structure of the surfactant. Thus, the cloud point increases with the number of ethoxy units and decreases with the length of the alkyl chain.

These nonionic surfactants are conventionally recorded as $C_iE_j$, i representing the number of carbon atoms in the alkyl chain and j representing the number of ethoxy groups.

The choice of the nonionic surfactant thus makes it possible to control the critical temperature of the heat-sensitive compound.

The second part of the heat-sensitive compound, which exhibits the property of complexing a chemical entity, for example a metal or a simple or complex metal ion, can have a monomeric, oligomeric or polymeric structure. It advantageously comprises an amino acid, a peptide, an oligopeptide or a polypeptide.

Mention may be made, as example of amino acid which can be used, of lysine, which makes it possible to complex uranium in the form of uranyl ions.

When the second part comprises an oligomer or a polymer other than an oligopeptide or a polypeptide, it can be a polymer comprising one or more complexing groups of the amine, amide or acid type, for example a polyamine, a polyamide or a polyacid.

By way of example, the second part can correspond to the following formula (III):

$$-CO-NH-(CH_2)_4-CH \begin{array}{c} \diagup NHCOR^1 \\ \diagdown COR^2 \end{array} \quad (III)$$

in which $R^1$ represents a hydrocarbonaceous group and $R^2$ represents a hydroxyl group, an alkoxy group or a nitrogenous group which may or may not be substituted.

The hydrocarbonaceous group used for $R^1$ preferably has from 1 to 10 carbon atoms; this hydrocarbonaceous group can be an alkyl group.

When $R^2$ represents a nitrogenous group, this group can correspond to one of the following formulae: $NH_2$, NHR and $NR_2$ with R representing a hydrocarbonaceous group, preferably an alkyl group, having from 1 to 10 carbon atoms.

When $R^2$ represents an alkoxy group, the latter preferably has 1 to 10 carbon atoms.

By way of example, $R^1$ can represent the methyl group and $R^2$ can represent the hydroxyl group or the methoxy group.

Mention may be made, as examples of heat-sensitive compounds in accordance with the invention, of:

the compound corresponding to the following formula (IV):

$$\begin{array}{c} C_iH_{2i+1} \\ \diagdown \\ CH-CO-NH-(CH_2)_4-CH \\ \diagup \\ HO-(CH_2CH_2O)_j \end{array} \begin{array}{c} \diagup NHCOR^1 \\ \diagdown COR^2 \end{array} \quad (IV)$$

in which i is equal to 12, j is equal to 4, $R^1$ represents $CH_3$ and $R^2$ represents $OCH_3$, and the compounds corresponding to the following formula (V):

$$C_iH_{2i+1}-(OCH_2CH_2)_j-OCH_2-CO-NH-(CH_2)_4-CH \begin{array}{c} \diagup NHCOR^1 \\ \diagdown COR^2 \end{array} \quad (V)$$

in which i is equal to 12, j is equal to 5, $R^1$ represents $CH_3$ and $R^2$ represents $OCH_3$ or OH.

The heat-sensitive compounds of the invention have the property of being soluble in water below the critical temperature $T_c$ and of becoming insoluble in water and soluble in oils (organic solvents, hydrocarbons) above this critical temperature.

The value of the critical temperature depends on the concentration of heat-sensitive compound and on the ionic strength of the medium.

As regards the concentration, it has little influence on the critical temperature of the heat-sensitive compounds of the invention. This is because the variations are less than 5° C. over a concentration range from 0.5 to 20% by weight.

As regards the ionic strength of the medium, the latter exerts a slightly stronger influence on the critical temperature $T_c$.

Thus, in the case where the medium comprises alkali metal nitrates, the critical temperature increases with the polarity of the alkali metal cation. This is reflected by an increase in the presence of lithium nitrate and a slight variation in the presence of sodium nitrate.

Preferably, the heat-sensitive compounds of the invention exhibit a critical temperature $T_c$ of 20 to 90° C. at a concentration of 0.1 to 25% by weight in aqueous solution.

According to the invention, the critical temperature $T_c$ of the compound can be controlled and adjusted by choosing a nonionic surfactant exhibiting an appropriate cloud point.

Thus, in the case of the compounds of formula (IV), where the alkyl chain is grafted in the α position and leaves the polyethoxylated group unsubstituted at the chain end, there is a large increase in the cloud point (50–55° C.) in comparison with the cloud point (6° C.) of the corresponding backbone $C_iE_j$ of the surfactant.

In contrast, in the case of the compounds of formula (V), where the alkyl chain is situated at the end of the polyethoxylated group, the cloud point is very close to that of the corresponding backbone $C_iE_j$.

When the compound corresponds to the formula (IV) given above, it exhibits a critical temperature $T_c$ of 55 to 75° C. at a concentration of 0.5 to 25% by weight in aqueous solution.

When the heat-sensitive compounds correspond to the formula (V) given above, they exhibit a critical temperature $T_c$ of 30 to 70° C. at a concentration of 0.1 to 25% by weight in aqueous solution.

Another subject-matter of the invention is a process for the preparation of a heat-sensitive compound having the property of being soluble in water below a critical temperature $T_c$ and insoluble in water above this temperature $T_c$, this property being thermally reversible, which comprises the reaction of a carboxylic derivative corresponding to one of the following formulae (VI) and (VIII):

(VI)

(VIII)

in which i is an integer ranging from 1 to 20, j is an integer ranging from 3 to 10 and $R^3$ represents Cl, OH or an alkoxy group, with a primary or secondary amine or polyamine comprising a group capable of complexing a chemical entity.

The primary or secondary amine or polyamine can be an amino acid or an amino acid derivative or can exhibit a peptide of nonpeptide structure.

According to a first embodiment of the invention, the process is used for the preparation of a compound corresponding to the following formula (IV):

(IV)

in which i is an integer ranging from 1 to 20, j is an integer ranging from 3 to 30, $R^1$ represents a hydrocarbonaceous group and $R^2$ represents a hydroxyl group, an alkoxy group or a nitrogenous group which may or may not be substituted, which comprises the reaction of a carboxylic derivative corresponding to the following formula (VI):

(VI)

in which i and j are as defined above and $R^3$ represents Cl, OH or an alkoxy group, with the lysine derivative corresponding to the following formula (VII):

(VII)

in which $R^1$ and $R^2$ are as defined above.

In this embodiment, the hydroxyl group of the carboxylic derivative of formula (VI) is preferably protected and the carboxyl group of this derivative is preferably activated before its reaction with the lysine derivative of formula (VII).

The hydroxyl group can be protected in the ether form, in particular via a molecule of the tetrahydropyran type. The carboxyl group can be activated using N-hydroxysuccinimide.

In this embodiment, the process additionally comprises a stage of deprotection of the hydroxyl group of the derivative of formula (VI) after reaction of the latter with the lysine derivative of formula (VII).

According to a second embodiment of the process of the invention which makes possible the preparation of a compound corresponding to the following formula (V):

(V)

in which i is an integer ranging from 1 to 20, j is an integer ranging from 3 to 30, $R^1$ represents a hydrocarbonaceous group and $R^2$ represents a hydroxyl group, an alkoxy group or a nitrogenous group which may or may not be substituted, the process comprises the reaction of a carboxylic derivative corresponding to the following formula (VIII):

(VIII)

in which i and j are as defined above and $R^3$ represents Cl, OH or an alkoxy group, with the lysine derivative corresponding to the following formula (VII):

(VII)

in which $R^1$ and $R^2$ are as defined above.

In the first embodiment of the process, the heat-sensitive compound can be obtained in five stages, from the polyoxyethylene glycol of formula HO—$(CH_2CH_2O)_j$—H, with overall yields of the order of 40%.

In the first stage, an alcohol functional group of the polyoxyethylene glycol is protected, for example using dihydropyran.

In the second stage, the polyoxyethylene glycol obtained in the first stage is reacted with a bromoalkanoic acid of formula $C_iH_{2i+1}$—CHBr—$CO_2H$ in order to obtain the carboxylated derivative of formula (VI) in which $R^3$ can represent a hydroxyl group (OH).

In the third stage, this carboxylic derivative is activated using N-hydroxysuccinimide.

In the fourth stage, the activated carboxylic derivative is reacted with the amine, the lysine derivative of formula (VII).

In the fifth stage, the hydroxyl functional group of the starting polyoxyethylene glycol is deprotected.

In the second embodiment of the process of the invention, the heat-sensitive compound can be obtained in two stages from the nonionic surfactant of formula $C_iH_{2i+1}$—$(OCH_2CH_2)_j$—OH by reaction of the latter with bromoacetic acid and then reaction of the carboxylated derivative with the amine, the lysine derivative of formula (VII).

The heat-sensitive compounds of the invention can be used to separate at least one chemical entity present in an aqueous solution.

Consequently, another subject-matter of the invention is a process for the extraction of at least one chemical entity present in an aqueous solution, in an aqueous single-phase system, which comprises the following stages:

a) a heat-sensitive compound as defined above is added to the aqueous solution at a temperature lower than the critical temperature $T_c$ of this compound, b) the reaction medium is brought to a temperature greater than the critical temperature $T_c$ of the compound in order to separate the reaction medium into two phases, respectively composed of a concentrated phase enriched in the chemical entity to be extracted, with a density greater than that of water, which sediments, and of a supernatant dilute aqueous phase depleted in the chemical entity, and c) the phase concentrated in the chemical entity is separated from the reaction medium.

According to the invention, the separation of this phase can be obtained in an aqueous single-phase system by simple separation by settling of the concentrated phase enriched in the chemical entity to be extracted.

According to an alternative embodiment of the extraction process, using a two-phase system, this process comprises the following stages:

a) a heat-sensitive compound as defined above and a water-immiscible organic phase are added to the aqueous solution at a temperature lower than the critical temperature $T_c$ of this compound, b) the reaction medium is brought to a temperature greater than the critical temperature $T_c$ in order to transfer the heat-sensitive compound and the chemical entity to be extracted into the organic phase, and c) the organic phase comprising the chemical entity is separated from the reaction medium.

The separation can thus be carried out in a liquid-liquid two-phase system by adding an organic liquid phase, for example an immiscible hydrocarbon, to the aqueous solution to be treated comprising the heat-sensitive compound at a temperature lower than $T_c$. Increasing the temperature of the reaction medium to a temperature greater than $T_c$ results in the transfer of the heat-sensitive compound and of the chemical entity complexed by this compound from the aqueous phase to the organic phase, which can subsequently be readily separated by simple settling.

The heat-sensitive compounds of the invention make it possible to complex, in a first stage, the chemical entity to be extracted and then to separate, in a second stage, the chemical entity/heat-sensitive compound complex by the simple action of an external stimulus: the increase in the temperature to a temperature greater than $T_c$.

In order to carry out the extraction process of the invention, use is made, in stage a), of an amount of heat-sensitive compound such that the concentration of heat-sensitive compound in the aqueous solution is from 0.1 to 25% by weight.

This process can be used to separate different chemical entities, in particular metals, such as actinides and lanthanides. It can be used in particular to extract uranium present in the form of the uranyl ion in an aqueous solution.

The invention has many advantages.

This is because the two-part structure of the heat-sensitive compounds used makes it possible to refine, on the other hand, the separation temperatures by the choice of the thermally reversible surfactant and, on the other hand, the complexing properties (both in terms of complexation constant and of selectivity with respect to a given entity) by the choice of the second complexing part.

Furthermore, for the extraction of the chemical entities, the heat-sensitive water-soluble compounds exhibit the following advantages:

1) the splitting of the two complexing and separation stages:

The solubility of the compounds in water makes it possible to introduce them directly into the aqueous phase to be treated. The complexing stage takes place in a homogeneous medium: its kinetics are therefore not limited by phenomena of diffusion and of interfacial contact, as in the case of the lipophilic extractants used in current separation processes in a liquid/liquid two-phase medium.

The duration of the complexing stage can be easily adjusted.

2) The separation is brought about by the action of an external stimulus: the increase in temperature.

3) The limitation of the volumes: the volume of phase enriched in chemical entity which sediments represents only a few % of the volume of the initial aqueous phase.

In terms of performance, the heat-sensitive water-soluble compounds developed here are effective in the separation of uranium in the form of the uranyl cation for low extractant/uranium molar ratios: 0.5 to 1. Their extraction capacities are greater than or of the same order of magnitude as those described with the heat-sensitive complexing polymers derived from PNIPAM.

The two-part structure of the compounds, which combines the two properties, complexing and thermal reversibility, in the same molecule, makes it possible to obtain an extraction performance which is much better than those obtained from mixtures of a thermally reversible surfactant and of a complexing agent.

Furthermore, the structure of the heat-sensitive compounds used can be optimized, in particular as regards the complexing properties.

The extraction performance can be improved:
1) by introducing, into the structure, a "strong" complexing agent specific for the chemical entity to be separated,
2) by developing oligomeric structures capable of mimicking, in a single molecule, the aggregates formed by conventional extractants. Mention may be made, among the oligomers targeted, of peptides or oligopeptides comprising, in their structure, at least one heat-sensitive unit of formula (I) or (II) and oligomers obtained by grafting a thermally reversible surfactant to an aminated or polyaminated macromolecular structure.

Figure 1:
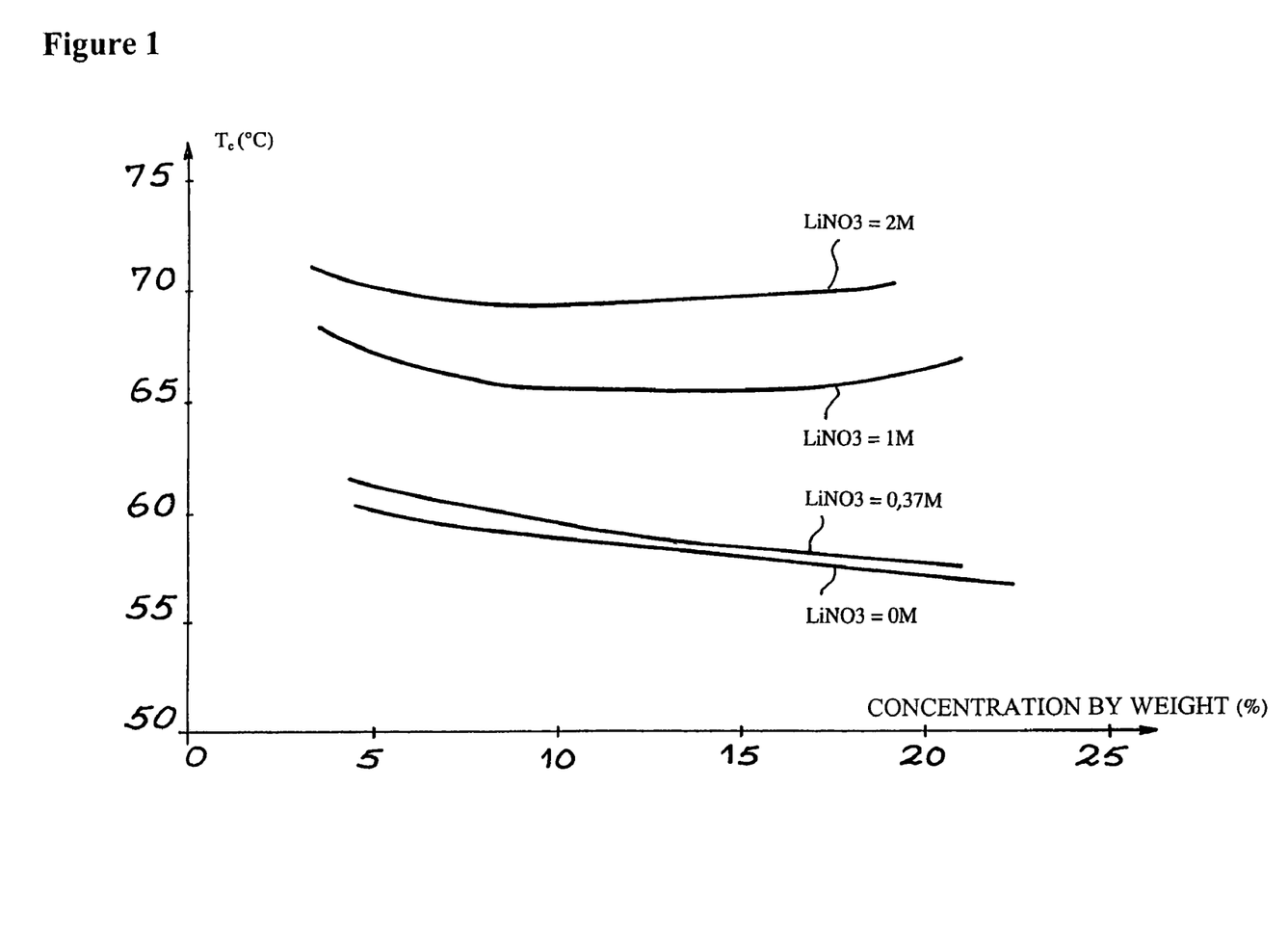
FIG. 1 illustrates, for several concentrations of $LiNO_3$ in an aqueous solution, the variation in the critical temperature $T_c$ (in °C.) of the compound 1a as a function of its concentration by weight (in %).

Other characteristics and advantages of the invention will become more clearly apparent on reading the description which follows of implementational examples given by way of illustration and without limitation, with reference to the single appended figure.

DETAILED ACCOUNT OF EMBODIMENTS

Example of the Synthesis of the Compound 1a:

The compound 1a is obtained in 5 stages from the corresponding polyethoxylated diol 2 according to the following reaction scheme:

In the first stage, an alcohol functional group of the polyoxyethylene glycol 2 is protected according to a reaction described by Philippon et al. [6] to give the alcohol 4. This alcohol 4 is subsequently condensed with 2-bromotetradecanoic acid 5 to give the acid 6: the synthesis is adapted from the procedure described by Wassermann et al. [7].

The acid 6 is activated by reaction with N-hydroxysuccinimide 7 according to a synthesis adapted from the procedure described by Popovitz-Biro et al. [8].

The activated ester 8 is subsequently condensed with N-acetyllysine 9 to give 10 according to a procedure adapted from the reference [8].

The heat-sensitive compound 1a is obtained after deprotection of the alcohol functional group of 10 and esterification according to a standard procedure [9].

The overall yield of the synthesis is 37%.

1st Stage: Preparation of the Compound 4 ($E_4THP$)

Tetraethylene glycol 2 (30 g, 163 mmol), dihydropyran 3 (7.8 g, 93 mmol) and para-toluenesulphonic acid PTSA (1.86 g, 10.8 mmol) are dissolved in 54 ml of dry tetrahydrofuran THF. The mixture is stirred at ambient temperature. The disappearance of 3 is monitored by thin layer chromatography TLC with dichloromethane $CH_2Cl_2$ as eluent. The plates are visualized with $H_2SO_4$. Under these conditions, 3 does not migrate and 4 has an $R_f$ of 0.39. Reaction is complete after 3 h 30. The PTSA is then neutralized with pyridine and the solvent is evaporated. The residue obtained is taken up in dichloromethane and washed twice with 20 ml of water and then once with saturated NaCl. The organic phase is dried over anhydrous $Na_2SO_4$ and then the solvent is evaporated.

The product 4 obtained (25 g) is purified twice (2×12.5 g) by chromatography on a silica column (350 g of silica, column with a diameter of 6 cm). The eluent used is composed successively of 100% ethyl acetate and then of an ethyl acetate 9/methanol 1 mixture.

Weight obtained=15.70 g; yield=61%.

Compound 4: [$E_4THP$]

Colourless oil $C_{13}H_{26}O_6$

MW=278 g/mol $^1$H NMR ($CDCl_3$): 4.6 ppm (t, 1H, O—C$\underline{H}$—O), 3.4–3.9 (m, 18H, OC$\underline{H_2}$C$\underline{H_2}$, $(CH_2)_3$—C$\underline{H_2}$—O), 1.5–1.8 (m, 6H, CH—(C$\underline{H_2}$)$_3$—$CH_2O$).

2nd Stage: Preparation of the Compound 6 [$C_{12}CH(CO_2H)E_4THP$]

The compound 4 $E_4THP$ (15.70 g, 56 mmol) and NaH (4.5 g of a 60% solution in a mineral oil, 187 mmol) are diluted in 40 ml of anhydrous THF (distilled over $CaH_2$) and the mixture is stirred at ambient temperature for 30 minutes while flushing with nitrogen. 2-Bromotetradecanoic acid (17.40 g, 56 mmol), in solution in 35 ml of THF, is added dropwise using a dropping funnel. The addition lasts one hour. The reaction mixture is then heated with an oil bath to 65° C. The reaction, monitored by TLC (eluent AcOEt 9/MeOH 1, visualization with iodine), is complete after 24 hours. The compound 6 shows virtually no migration and the $R_f$ of the compound 4 is 0.57. The mixture is taken up in 40 ml of ether and then washed 4 times with 250 ml of 1N HCl. The aqueous phase is subsequently washed with ether. The organic phases are combined and then washed once with 30 ml of NaCl to pH 6. The organic phase obtained is dried over anhydrous $Na_2SO_4$. After evaporating the solvent, 28 g of crude product 6 are recovered.

2.5 g of crude product 6 are purified by chromatography on a silica column (100 g) with an increasing elution gradient: AcOEt/MeOH: 4/1 then 1/1. 1.8 g of pure compound 6 are recovered.

Yield =72%.

Compound 6: [$C_{12}CH(CO_2H)E_4THP$]

Yellow oil $C_{27}H_{52}O_8$

MW=504 g/mol $^1$H NMR ($CDCl_3$): 4.6 ppm (t, 1H, O—C$\underline{H}$—O), 3.4–4.1 (m, 19H, OC$\underline{H_2}$C$\underline{H_2}$, $(CH_2)_3$—C$\underline{H_2}$OCH, $(OCH_2CH_2)_5$—C$\underline{H}$), 1.1–2.4 (m, 28H, (C$\underline{H_2}$)$_{11}$), 0.9 (t, 3H, C$\underline{H_3}$$(CH_2)_{11}$).

3rd Stage: Preparation of the Compound 8 [$C_{12}CH(CO_2NHS)E_4THP$].

The compound 6 (12.9 g, 25.72 mmol), N-hydroxysuccinimide (3.22 g, 28.29 mmol) and N-(3-dimethyl-aminopropyl)-N'-ethylcarbodiimide hydrochloride EDC (5.5 g, 28.29 mmol) are dissolved in 30 ml of dichloromethane over a molecular sieve. The reaction is monitored by TLC with the eluent AcOEt 2/MeOH 1, with visualization by $H_2SO_4$. Under these conditions, the compound 6 has an $R_f$ of 0.50 and the compound 8 has an $R_f$ of 0.66. The mixture is stirred for one hour in an ice bath and then for 20 hours at ambient temperature. The mixture is then filtered through celite in order to remove the molecular sieve and the solvent is evaporated. The mixture is taken up in dichloromethane and washed once with 1N HCl and then 4 times with saturated NaCl to pH 6. 15.4 g of product are thus obtained and are used without additional purification in the following stage.

Quantitative yield.

Compound 8: [$C_{12}CH(CO_2NHS)E_4THP$]

Yellow oil $C_{31}H_{55}O_{10}N$

MW=601 g/mol $^1$H NMR ($CDCl_3$): 3.4–3.7 ppm (m, 19H, OC$\underline{H_2}$C$\underline{H_2}$, $(OCH_2CH_2)_5$—C$\underline{H}$, $(CH_2)_3$—C$\underline{H_2}$OCH), 1.2–1.9 (m, 28H, (C$\underline{H_2}$)$_{11}$—, (C$\underline{H_2}$)$_3$—$CH_2OCH$), 0.9 (t, 3H, C$\underline{H_3}$$(CH_2)_{11}$—).

4th Stage: Preparation of the Compound 10 [$C_{12}CH(COAcLysCO_2H)E_4THP$]

The crude compound 8 (2.0 g, 3.33 mmol) is dissolved in 40 ml of acetone. N-Acetyllysine $AcLysCO_2H$ (1.25 g, 6.66 mmol) and triethylamine (1.9 ml, 13.32 mmol), dissolved in 20 ml of water, are added to the reaction medium. Monitoring by TLC is carried out with the eluent AcOEt 4/MeOH 1/NH$_3$ 0.5 (visualization with ninhydrin and then with $H_2SO_4$). The compound 8 has an $R_f$ of 0.84 and the compound 10 has an $R_f$ of 0.59. After stirring at ambient temperature for 20 hours, the reaction is halted by addition of trifluoroacetic acid and the acetone is evaporated. The mixture is taken up in 20 ml of dichloromethane. The excess acetyllysine is removed by extraction with 15 ml of a 1N HCl solution. The organic phase obtained is washed with 4×35 ml of a saturated NaCl solution to pH 5. After drying over $Na_2SO_4$ and evaporating the solvent, 2.0 g of analytically pure compound 10 are recovered.

Yield=89%

Yellow oil $C_{35}H_{66}O_{10}N_2$

MW=674 g/mol

$^1$H NMR (CDCl$_3$): 4.63 ppm (t, 1H, O—C$\underline{H}$—O), 3.4–3.9 (m, 22H, OC$\underline{H_2}$(CH$_2$)$_3$, (CH$_2$)$_{11}$—C$\underline{H}$—, (C$\underline{H_2}$)NH—, (OC$\underline{H_2}$CH$_2$)$_4$, (CH$_2$)$_4$—C$\underline{H}$(CO$_2$H)N—), 2.0 (s, 3H, COC$\underline{H_3}$), 1.1–1.6 (m, 34H, (C$\underline{H_2}$)$_{11}$—, (C$\underline{H_2}$)$_3$—CH$_2$OCH, NH—CH$_2$(C$\underline{H_2}$)$_3$), 0.9 (t, 3H, (CH$_2$)$_{11}$—C$\underline{H_3}$).

$^{13}$C NMR (CDCl$_3$): 173.25–173.5 ppm (C$^{14}$-C$^{33}$), 98.65 (C$^{23}$), 66–70 (C$^{15-22}$), 61.9 (C$^{15-22}$), 52.9 (C$^{32}$), 51.9–32.74–31.47 (C$^{28}$), 28.7–30.4–21.48–19.06 (C$^{24-26}$, C$^{28}$, C$^{2-12}$), 13.67 (C$^1$).

5th Stage: Synthesis of the Compound 1a [C$_{12}$CH(AcLysCO$_2$Me)E$_4$]

The compound 10 (1.5 g, 2.22 mmol) and PTSA (0.76 g, 4.44 mmol) are dissolved in 10 ml of methanol. The mixture is stirred at ambient temperature. Monitoring by TLC is carried out with the eluent AcOEt 4/MeOH 1/NH$_3$0.5 (visualization with ninhydrin and then with H$_2$SO$_4$). The compound 1a has an R$_f$ of 0.72. The reaction is complete after 5 hours. The methanol is then evaporated. The mixture is taken up in 15 ml of dichloromethane and washed with 3×20 ml of a saturated NaCl solution to neutral pH, in order to remove the excess PTSA. After drying over Na$_2$SO$_4$ and evaporating the solvent, 1.2 g of product are recovered.

Yield=89%
Yellow oil
C$_{31}$H$_{60}$O$_9$N$_2$
MW=604 g/mol $^1$H NMR (CDCl$_3$): 7.3 ppm (d, NH (2)), 6.5 ppm (t, NH (1)), 4.51 ppm (1H, C$^{27}\underline{H}$), 3.2–3.9 ppm (m, 22H, (CH$_2$)$_{11}$—C$\underline{H}$, C$\underline{H_2}$—N—, (OC$\underline{H_2}$C$\underline{H_2}$)$_4$, CO$_2$C$\underline{H_3}$), 2.0 ppm (s, 3H, NHCOC$\underline{H_3}$), 1.2–1.8 ppm (m, 28H, (C$\underline{H_2}$)$_{11}$—, NH—CH$_2$(C$\underline{H_2}$)$_3$), 0.9 ppm (t, 3H, (CH$_2$)$_{11}$—C$\underline{H_3}$).

$^{13}$C NMR (CDCl$_3$): 172.82 ppm (CO), 172.79 ppm (CO), 172.65 ppm (CO), 172.58 ppm (CO), 144.58 ppm, 122.96 pp–80.7 ppm–69.3–72.0 ppm (C15–22), 61.17–61.27 ppm (C15–22), 52.9 ppm (C27), 5.1.31–51.91 ppm (C29), 38.0 ppm (C23), 21.16–31.45 ppm (C2–12, C24–26) -13.66 ppm (C1).

MS (ESI K$^+$/MeOH), m/z: 643 (MK$^+$, 100%), 473 (20%), 303 (7.5%).

IR (cm$^{-1}$): 3062 (OH), 2921 (CH), 1744 (CO), 1654 (HNCO), 1539 (NH), 1108 (COC).

|   | % exp. | % calc. |
|---|---|---|
| C | 61.84 | (61.56) |
| H | 10.35 | (10.00) |
| N | 4.30 | (4.63) |
| O | 23.21 | (23.81) |

Quantitative determination of the traces of ions by capillary electrophoresis:

Analysis of the cations by capillary electrophoresis in electrokinetic injection mode (internal standard: NH$_4^+$ ions) shows that the product comprises a small amount of Na$^+$ ions: on average 0.8 mol % (i.e. 0.03% by weight). Another batch of 4 g of the compound 1a was synthesized from the compound 8 by following the same procedure for Stages 4 and 5. This batch comprises 1.3 mol % of Na$^+$ ions (i.e. 0.05% by weight). All the physicochemical experiments were carried out on the latter batch.

Physicochemical Properties of the Compound 1a:

1) Measurement of the Density

The density of the compound 1a, determined using an Anton Paar densimeter, is 0.950 at 25° C.

2) Determination of the Critical Micelle Concentration (cmc) and of the Surface Area Per Polar head: Curve γ=f(log C) Obtained by the Du Nouy Ring Method The cmc and the surface area per polar head of the compound 1a were deduced from surface tension measurements carried out on a Krüss Digital Tensiometer K 10. The results are given in Table 1 below and are compared with the values characteristic of the nonionic surfactants C$_{12}$E$_5$ (C$_{12}$H$_{25}$—(OCH$_2$CH$_2$)$_5$—OH) and C$_{12}$E$_4$(C$_{12}$H$_{25}$—(OCH$_2$CH$_2$)$_4$—OH), which are drawn from the literature ([10]).

TABLE 1

Comparison of the cmc, $\gamma_{cmc}$ and $\sigma_s$ values of C$_{12}$E$_4$, C$_{12}$E$_5$ and the compound 1a

| Compound | cmc (mol · l$^{-1}$) | $\gamma_{cmc}$ (mN · m$^{-1}$) | $\sigma_s^{(c)}$ (Å$^2$) |
|---|---|---|---|
| C$_{12}$E$_5$$^{(a)}$ | 9.4 ± 0.5 × 10$^{-5}$ | 29.2 | 51 ± 2 |
| C$_{12}$E$_4$$^{(b)}$ | 10.6 × 10$^{-5}$ [10] | / | 45 [10] |
| 1a | 4.9 ± 0.5 × 10$^{-5}$ | 33.1 | 60 ± 2 |

(a) values determined experimentally; (b) values given in the literature [10]; (c): area of the molecule at the water/air interface in (angstroms)$^2$.

3) Determination of the Critical Temperature T$_c$ of the Compound 1a: Phase Separation Curves of the Water/Surfactant Systems The phase separation curves of the water/1a and water/C$_{12}$E$_5$ systems were drawn up. The compound 1a exhibits a critical temperature of 57±1° C.

For comparison, the nonionic surfactants C$_{12}$E$_4$ and C$_{12}$E$_5$ have a critical temperature of 6° C. [5] and 29° C. The functionalization thus greatly increases the critical temperature in comparison with C$_{12}$E$_4$, thus demonstrating a strong hydrophilic contribution of the grafted amino acid residue.

4) Influence of the Ionic Strength on the Phase Separation Curve of the Water/Compound 1a System The influence of the ionic strength on the critical temperature of 1a was determined by drawing up the phase separation curves of aqueous solutions of 1a in the presence of variable concentrations of $LiNO_3$.

FIG. 1, which illustrates the variation in the critical temperature $T_c$ (in ° C.) as a function of the concentration by weight of 1a (%), shows that the critical temperature increases with the concentration of $LiNO_3$ and varies little with the concentration of 1a.

Table 2 makes it possible to compare the critical temperatures $T_c$ at different concentrations of $LiNO_3$ for a fixed concentration of 1a ($4.9 \times 10^{-2}$ mol.l$^{-1}$, i.e. approximately 3% by weight).

TABLE 2

| [LiNO$_3$] (M) | $T_c$ (° C.) |
|---|---|
| 4.4 | 74.9 |
| 2 | 71.5 |
| 1 | 69.3 |
| 0.63 | 68.6 |
| 0.37 | 62.9 |
| 0 | 60.6 |

The increase in $T_c$, salting-in effect, in the presence of $LiNO_3$ is an effect which is already known and which is characteristic of surfactants of $C_iE_j$ type [11]. At low $LiNO_3$ concentrations, the effect is not very marked. At higher concentrations, from 0.6M, this effect becomes more significant and the critical temperature $T_c$ then increases approximately proportionally to the $LiNO_3$ concentration.

EXAMPLE 2

Synthesis of the Compound 2a

The compound 2a is obtained in two stages from the surfactant $C_{12}E_5$ (compound 11) according to the following scheme:

In the first stage, the surfactant 11 $C_{12}E_5$ is converted to the acid 13 by reaction with bromoacetic acid 12. The compound 2b is subsequently obtained by coupling the acid 13 to the methyl ester of N-acetyllysine 9. The overall yield of the synthesis, with respect to $C_{12}E_5$, is approximately 65%.

Preparation of the Compound 9: Ac-Lys(NH$_2$)-OMe (This Compound is Commercially Accessible)

1.67 g of $SOCl_2$ ($1.4 \times 10^{-2}$ mol) are added under a stream of nitrogen to a 100 ml two-necked round-bottomed flask comprising 20 ml of dry methanol cooled to 0° C. 0.74 g of N-acetylated lysine (Ac-Lys(NH$_2$)—OH, $4 \times 10^{-3}$ mol) is rapidly introduced under a stream of nitrogen into the reaction medium and is then left stirring at ambient temperature for 12 hours. The progress of the reaction is monitored by TLC with a chloroform/methanol/acetic acid 5/3/1 mixture as eluent and ninhydrin as visualizaton agent. Under these conditions, the N-acetyllysine has an $R_f$ of 0.07 and the ester 9 has an $R_f$ of 0.43.

Before isolating the product, the reaction medium is neutralized with $NaHCO_3$ and then the excess methanol is evaporated on a rotary evaporator. The crude product then obtained is subsequently diluted in dry ethanol for the purpose of removing the residual salts by centrifuging. After concentrating the supernatant and drying under reduced pressure, 0.647 g of product 9 ($3.2 \times 10^{-3}$ mol) is isolated.

Yield: 80%

Characteristics of the compound 9:

Oily appearance

MW=202.2 g/mol $^1$H NMR (D$_2$O): 4.24–4.19 ppm (m, 1H, C$\underline{H}$), 3.59 ppm (s, 3H, OC$\underline{H}_3$), 2.825 ppm (t, 2H, —CH$_2$—C$\underline{H}_2$—NH$_2$), 1.87 ppm (s, 3H, —NHCOC$\underline{H}_3$), 1.75–1.24 ppm (m, 6H, CH—(C$\underline{H}_2$)$_3$—CH$_2$—NH$_2$).

1st Stage: Preparation of the Compound 13 [$C_{12}E_5$-O—CH$_2$—COOH]

A suspension of NaH cleaned beforehand from its mineral oil ($3.45 \times 10^{-2}$ mol, 60% by weight, 1.38 g, diluted in 10 ml of anhydrous THF) is introduced under a stream of nitrogen into a 100 ml three-necked round-bottomed flask surmounted by a reflux condenser and equipped with a nitrogen inlet. The compound 11 $C_{12}E_5$ ($9.86 \times 10^{-3}$ mol, 4 g), diluted in 10 ml of anhydrous THF, is added under a stream of nitrogen. The reaction medium is left stirring at ambient temperature for 30 minutes under a stream of nitrogen. Bromoacetic acid 12 ($1.48 \times 10^{-2}$ mol, 2.07 g), diluted in 7 ml of anhydrous THF, is subsequently introduced gradually using a dropping funnel. The addition time extends over 30 minutes in order to compensate for the release of heat brought about by the substitution reaction. The reaction medium is subsequently heated at 60° C. for 12 hours. The progress of the reaction is monitored by TLC with an AcOEt/MeOH (4/1) mixture as eluent and H$_2$SO$_4$ as visualization agent: $R_f$ of 11 ($C_{12}E_5$)=0.8 and $R_f$ of 13=0.2. On completion of the reaction, the THF is evaporated on a rotary evaporator and the crude mixture is taken up in ether. Extraction with ether and 1N hydrochloric acid makes it possible, after washing the organic phase 3 times, drying the latter over $MgSO_4$ and evaporating the ether, to recover 4.30 g ($9.26 \times 10^{-3}$ mol) of product 13 freed from any impurity.

Yield: 94%

Characteristics of the product 13:

$$C_{12}H_{25}-O-(CH_2CH_2O)_5-CH_2COOH \quad 13$$

Yellow oil

MW: 464 g/mol $^1$H NMR ($CDCl_3$): 4.09 ppm (s, 2H, $C_{12}E_5$-O—C$\underline{H}_2$—COOH), 3.66–3.52 ppm (m, 20H, O—(C$\underline{H}_2$—C$\underline{H}_2$)$_5$—O), 3.39 ppm (t, 2H, $C_{11}H_{23}$—C$\underline{H}_2$—O—), 1.5 ppm (m, 2H, $C_{10}H_{21}$—C$\underline{H}_2$—CH$_2$—O), 1.19 ppm (s, 18H, $C_9\underline{H}_{18}$), 0.81 ppm (t, 3H, $CH_3$).

2nd Stage: Preparation of the Compound 2a 1.22 g of the compound 13 ($2.637 \times 10^{-3}$ mol) are dissolved in 100 ml of dry DMF in a 250 ml two-necked round-bottomed flask equipped with a magnetic bar and a nitrogen inlet. 1.246 g of 1-hydroxybenzotriazole HOBT ($9.232 \times 10^{-3}$ mol) and then 0.64 g of the compound 9 ($3.16 \times 10^{-3}$ mol) are added under a stream of nitrogen. After stirring at ambient temperature for 15 minutes, 1.265 g of N-(3-dimethylaminopropyl)-N'-ethylcarbodiimide hydrochloride EDC ($6.6 \times 10^{-3}$ mol) are introduced. The reaction medium is subsequently left stirring at ambient temperature for 12 hours. Monitoring of the reaction is carried out by TLC with an AcOEt/MeOH 1/1 eluent and $H_2SO_4$ as the visualization agent. Under these conditions, the acid 13 has an $R_f$ of 0.3 and the product 2a has an $R_f$ of 0.7. After evaporating the DMF, the crude product is taken up in dichloromethane and washed 3 times with 1N HCl. After drying over $MgSO_4$ and evaporating the dichloromethane, 1.56 g of the crude product 2a are obtained (Yd: 91%). The product 2a is purified by chromatography on a silica column (diameter 3.5 cm, 80 g of $SiO_2$) with an AcOEt/MeOH 6/1 eluent. 1.2 g ($1.851 \times 10^{-3}$ mol) of the pure product 2a are recovered.

Yield: 70%

Characteristics of the product 2a:

Oil possessing yellow glints

MW: 648.2 g/mol

2a $$\begin{array}{c} O \\ \parallel \\ CH_3-C-HN-CH-CO_2Me \\ | \\ (CH_2)_4 \\ | \\ NH \\ | \\ C_{12}H_{25}-O-(CH_2CH_2O)_4-CH_2CH_2O-CH_2-CO \end{array}$$

$^1$H NMR ($CDCl_3$): 7.10 ppm (t, 1H, $CH_2CO$—N$\underline{H}$—($CH_2$)$_4$—), 6.33 ppm (d, 1H, $CH_3CO$—N$\underline{H}$—CH—), 4.56–4.50 ppm (m, 1H, —HN—CH($CH_2$)$_4$—$CO_2$Me), 3.98 ppm (s, 2H, $C_{12}E_5$-O—C$\underline{H}_2$—CO(NH)—), 3.73 ppm (s, 3H, OM$\underline{e}$), 3.66–3.55 ppm (m, 20H, O—(C$\underline{H}_2$—C$\underline{H}_2$)$_5$—O), 3.44 ppm (t, 2H, $C_{11}H_{23}$—C$\underline{H}_2$—O—), 3.28 ppm (m, 2H, —CO—NH—C$\underline{H}_2$—(CH$_2$)$_3$—), 2.02 ppm (s, 3H, C$\underline{H}_3$—CO—NH—), 1.80–1.25 ppm (m, 26H, —CH—(C$\underline{H}_2$)$_3$—$CH_2$—$NH_2$, $C_{10}H_{21}$—C$\underline{H}_2$—CH$_2$—O—, $H_3C$—$C_9\underline{H}_{18}$—CH$_2$—), 0.87 ppm (t, 3H, $\underline{H}_3C$—$C_9H_{18}$—CH$_2$—).

EXAMPLE 3

Synthesis of the Compound 2b

The compound 2b is obtained in 3 stages from the surfactant $C_{12}E_5$, compound 11, according to the following scheme:

$$C_{12}E_5 \longrightarrow C_{12}H_{25}-(OCH_2CH_2)_5-OCH_2-CO_2H \longrightarrow$$
11
13

$$C_{12}H_{25}-(OCH_2CH_2)_5-OCH_2-CO_2-N\text{(succinimide)}$$
14

$$C_{12}H_{25}-(OCH_2CH_2)_5-OCH_2-CONHS \quad +$$
14

$$H_2N-(CH_2)_4-CH\begin{array}{l}NHCOCH_3 \\ CO_2H\end{array} \longrightarrow$$
15

$$C_{12}H_{25}-(OCH_2CH_2)_5-OCH_2-CO-NH-(CH_2)_4-CH\begin{array}{l}NHCOCH_3 \\ CO_2H\end{array}$$
2b The first stage consists of the conversion of the surfactant $C_{12}E_5$ 11 to the acid 13 according to the protocol described above (synthesis of 2a). The acid 13 is activated in the form of the ester of N-hydroxysuccinimide 14. Finally, the third stage, which results in 2b, consists of a coupling of the activated ester 14 with N-acetyllysine 15. The overall yield of the synthesis, with respect to $C_{12}E_5$, is 80%.

1st Stage: Preparation of the Compound 14 [$C_{12}E_5$-O—$CH_2$—CO—NHS]

4.18 g of the compound 13 ($9 \times 10^{-3}$ mol) are dissolved in 40 ml of anhydrous $CH_2Cl_2$ in a 100 ml two-necked round-bottomed flask provided with a nitrogen outlet and a magnetic stirrer. The temperature of the reaction medium being lowered to 0° C., 2 g of EDC ($1.08 \times 10^{-2}$ mol) are introduced under a stream of nitrogen. After stirring at 0° C. for 30 minutes, N-hydroxysuccinimide ($1.35 \times 10^{-2}$ mol, 1.554 g) is introduced. The reaction medium is subsequently stirred at 0° C. for 1 hour and then at ambient temperature for 12 hours. The reaction is monitored by TLC with an AcOEt/MeOH 2/1 eluent and $H_2SO_4$ as visualization agent: the $R_f$ values are respectively 0.12 for the compound 11 and 0.8 for the compound 14. The reaction medium is washed twice with 1N HCl. The organic phase is dried over $MgSO_4$ and then concentrated on a rotary evaporator. The activated ester 14 is obtained with a yield of 91% ($8.2 \times 10^{-3}$ mol, 4.59 g) and is used without additional purification in the following stage.

Characteristics of the product 14:

Yellow oil

MW: 561 g/mol

14

$$C_{12}H_{25}-O-(CH_2CH_2O)_5-CH_2\overset{O}{\underset{\parallel}{C}}-O-N\text{(succinimide)}$$

$^1$H NMR ($CDCl_3$): 4.47 ppm (s, 2H, O—C$\underline{H}_2$—COON—), 3.75–3.52 ppm (m, 20H, O—(C$\underline{H}_2$—C$\underline{H}_2$)$_5$—O), 3.40 ppm (t, 2H, $C_{11}H_{23}$—C$\underline{H}_2$—O—), 2.80 ppm (s, 4H, N—CO—CH$_2$—CH$_2$—CO), 1.5 ppm (m, 2H, C$_{10}$H$_{21}$CH$_2$—CH$_2$—O—), 1.21 ppm (s, 18H, H$_3$C—C$_9$H$_{18}$), 0.82 ppm (t, 3H, CH$_3$).

The presence of a small amount of impurity at 2.82 ppm is observed in the spectrum.

IR (cm$^{-1}$): 1741 (C=O ester), 1784.10 (C=O imide)

2nd Stage: Preparation of the Compound 2b

The ester 14 (4.06×10$^{-3}$ mol, 2.28 g) is dissolved in 60 ml of acetone. N-Acetyllysine 15 (6.1×10$^{-3}$ mol, 1.148 g) and triethylamine (2.03×10$^{-2}$ mol, 2.054 g), in solution in 25 ml of ultrapure water, are added to the reaction medium at ambient temperature. After reacting at ambient temperature for 12 hours, the acetone is evaporated and then the mixture is taken up in dichloromethane. Extraction with 1N HCl and CH$_2$Cl$_2$ makes it possible to remove all the residual products (excess of Ac-Lys-(OH), triethylamine, N-hydroxysuccinimide). The organic phase is then dried over MgSO$_4$ and the solvent is removed under reduced pressure.

2.445 g of heat-sensitive compound 2b (3.857×10$^{-3}$ mol) are obtained.

Yield=95%

Characteristics of the compound 2b:

Yellow oil

MW: 634.2 g/mol

2b $^1$H NMR (CDCl$_3$): 7.39 ppm (t, 1H, CH$_2$—CO—N H—(CH$_2$)$_4$—), 6.81 ppm (d, 1H, CH$_3$CO—NH—CH—), 4.58 ppm (m, 1H, —HN—CH(CH$_2$)$_4$—CO$_2$H), 4.02 ppm (s, 2H, C$_{12}$E$_5$-O—CH$_2$—CO(NH)—), 3.76–3.57 ppm (20H, O—(CH$_2$—CH$_2$)$_5$—O), 3.45 ppm (t, 2H, C$_{10}$H$_{20}$—C H$_2$—O—), 3.36 ppm (m, 2H, —CO—NH—C H$_2$—(CH$_2$)$_3$—), 2.05 ppm (s, 3H, CH$_3$—CO—), 1.87–1.22 ppm (m, 26H, —CH—(CH$_2$)$_3$—CH$_2$—NH$_2$, C$_{10}$H$_{21}$—C H$_2$CH$_2$—O—, H$_3$C—C$_9$H$_{18}$—CH$_2$—), 0.88 ppm (t, 3H, C H$_3$—CH$_2$—).

The presence of a small amount of an impurity at 2.85 ppm is observed in the spectrum.

Critical Temperatures of the Compounds 2a and 2b

The critical temperatures of the compounds 2a and 2b are 38 and 40° C. respectively: they are slightly greater than that of the grafted nonionic surfactant C$_{12}$E$_5$ (30° C.)

The values of the critical temperatures of the compounds 2a and 2b in water and in the presence of alkali metal nitrates (NaNO$_3$ or LiNO$_3$) are listed in Table 3 below:

TABLE 3

| Compound | Concentration by weight | Concentration M | [NaNO$_3$] M | [LiNO$_3$] M | T$_c$ (° C.) +/-2° C. |
|---|---|---|---|---|---|
| 2a | 2.6% | 0.04 | 0 | 0 | 38 |
| 2a | 2.3% | 0.036 | 0 | 4 | 66 |

TABLE 3-continued

| Compound | Concentration by weight | Concentration M | [NaNO$_3$] M | [LiNO$_3$] M | T$_c$ (° C.) +/-2° C. |
|---|---|---|---|---|---|
| 2a | 3% | 0.046 | 1 | 0 | 48 |
| 2a | 3% | 0.046 | 2 | 0 | 35 |
| 2h | 3% | 0.047 | 0 | 0 | 40 |
| 2b | 3% | 0.047 | 1 | 0 | 39 |
| 2h | 3% | 0.047 | 2 | 0 | 35 |

EXAMPLE 4

Extraction of Uranium, in the Form of Uranyl U(VI) Nitrate, by the Compounds 1a and 2a by Varying the Temperature The experiments are carried out by introducing, in aqueous solution, the water-soluble, heat-sensitive and thermally reversible compound (1a or 2a), lithium nitrate and uranyl nitrate in variable respective concentrations. The critical temperature is determined for each composition. The rise in the temperature slightly above the critical temperature T$_c$ (a few degrees) brings about the separation of the two phases, a low-volume concentrated phase enriched in the uranyl ion and with a density greater than water, which sediments, and a supernatant dilute phase depleted in the uranyl ion. After natural separation by settling, the content of U(VI) remaining in the supernatant phase is determined.

The concentrations of uranyl nitrate are determined in the aqueous phase before and after the critical temperature by X-ray fluorescence (line situated between 11.8 and 14.8 keV).

The results of the experiments are listed in Table 4. They show that the heat-sensitive compounds 1a and 2a make it possible to efficiently separate the uranyl ion by simple variation in temperature with extraction yields ranging up to 45%, this being achieved in the presence of stoichiometric or substoichiometric amounts of compound 1a or 2a. In a single separation stage, the extraction capacities reach 0.35–0.4 mol of U per mole of heat-sensitive compound.

By way of comparison, the results obtained with the simple nonionic surfactant C$_{12}$E$_5$ and with a mixture of the nonionic surfactant C$_{12}$E$_5$ and of a lysine derivative, the methyl ester of N,N'-diacetylated lysine LysNAcOMe, have also been given in Table 4.

In both these cases, the separation of the uranium is negligible. This clearly demonstrates the advantage of the heat-sensitive compounds of the invention and of their structure as two parts having different functions, the first part making it possible to easily provide the separation and the second part providing the complexing of the chemical entities to be separated.

The results in Table 4 also show that the compound 1a, comprising a pendant polyethoxylated chain with a free hydroxyl, group, has greater extraction capacities than those of the compound 2a, for which the complexing amino acid residue is grafted via the end of the polyethoxylated group.

For a fixed concentration of lithium nitrate, the phase separation temperatures (cloud point) decrease in the presence of the uranyl cation with an effect which becomes greater as the uranyl/heat-sensitive compound ratio increases. Furthermore, the comparison of the critical temperatures and of the amounts of uranium extracted for the compounds 1a and 2a shows that the decrease in the critical temperature becomes greater as the amount of uranium extracted increases: the fall in T$_c$ thus appears to result from the complexing of the uranyl cation by the compound.

TABLE 4

| Compound concentration (M) | [LiNO$_3$] M | [UO$_2^{2+}$]$_{init}$[a] | T$_c$ °C. | [UO$_2^{2+}$]$_{remaining}$[b] M | U extracted[c] % | U extracted/compound[d] mol/mol | U extracted/compound[d] mol/g |
|---|---|---|---|---|---|---|---|
| I    | 1a: 0.04 M | 0 | 0 | 70 | — | — | — | — |
| II   | 1a: 0.0044 M | 4 | 0 | 77 | — | — | — | — |
| III  | 1a: 0.004 M | 4 | 0.021 | 26 | 0.012 | 43% | 0.22 | 3.7 × 10$^{-4}$ |
| IV   | 1a: 0.043 M | 4 | 0.028 | 24 | 0.018 | 36% | 0.23 | 3.9 × 10$^{-4}$ |
| V    | 1a: 0.04 M | 4 | 0.041 | ~0 | 0.026 | 36% | 0.37 | 6.2 × 10$^{-4}$ |
| VI   | 1a: 0.04 M | 2 | 0.022 | <80 | 0.012 | 45% | 0.25 | 4.1 × 10$^{-4}$ |
| VII  | 2a: 0.04 M | 0 | 0 | 38 | — | — | — | — |
| VIII | 2a: 0.036 M | 4 | 0 | 66 | — | — | — | — |
| IX   | 2a: 0.043 M | 4 | 0.021 | 51 | 0.016 | 24% | 0.12 | 1.8 × 10$^{-4}$ |
| X    | 2a: 0.042 M | 4 | 0.038 | 41 | 0.032 | 16% | 0.14 | 2.2 × 10$^{-4}$ |
| | | | | Reference test | | | | |
| XI   | C$_{12}$E$_5$[e]: 0.04 M | 2 | 0.027 | 38 | 0.026 | <3% | <0.025 | <6 × 10$^{-5}$ |
| XII  | C$_{12}$E$_5$: 0.04 M + LysNAcOMe[f]: 0.04 M | 2 | 0.22 | 38 | 0.022 | ~0 | ~0 | ~0 |

[a] initial concentration of uranyl nitrate;
[b] concentration of uranyl remaining in the supernatant phase after separation;
[c] percentage of uranyl extracted, calculated while ignoring the variations in volume: [U]$_{init}$ − [U]$_{remaining}$/[U]$_{init}$;
[d] expressed with respect to the amount of compound initially introduced;
[e] C$_{12}$E$_5$: C$_{12}$H$_{25}$—(OCH$_2$CH$_2$)$_5$—OH
[f] LysNAcOMe: methyl ester of N,N'-diacetylated lysine

REFERENCES CITED

[1] Bergbreiter D. E., Koshti N., Franchina J. G., Frels J. G., Angew. Chem. Int. Ed., 39, 2000, 1040–2,
[2] Takeshita K. and Nakano Y., Solvent Extraction and Ion Exchange, 18(2), 2000, 375–86,
[3] Hinze W. L., Pramauro E., Critical Reviews in Analytical Chemistry, 24(2), 1993, 133–77,
[4] Tani H., Kamidate T., Watanabe H., J. Chromatogr. A, 780, 1997, 229–241,
[5] Huibers P. D. T., Shah D. O., Katrizky A. R., J. Colloid and Interface Sci., 193, 1997, 132–6,
[6] Philippon A., Tao J., Tétard D., Degueil-Castaing M., Maillard B., Synthetic Commun., 27(15), 1997, 2651–2682,
[7] Wassermann H., Azim E., Coudert G., Achilefii S., Selve C., J. Chem. Soc. Perkin Trans. 2, 1992, 2043–2047.
[8] Popovitz Biro R., Hill K., Shavit E., Hung D. J., Lahav M., Leiserowitz L., Sagiv J., Hsiung H., Meredith G. R., Vanherzeele F L, J. Amer. Chem. Soc., 112, 1990, 2498–2506.
[9] P. J. Kocienski, Protecting Groups, Georg Thieme Verlag, Stuttgart, N.Y., 1994, pp. 83–87.
[10] Grillo Isabelle, Thesis of the University Paris XI (1998), p. 175.
[11] Schott H., Kyu Han S., J. Pharmaceutical Sci., 64 (4), 1975, 658–664.
[12] U.S. Pat. No. 4,154,674
[13] WO-A-00/73521.

The invention claimed is:

1. A heat-sensitive compound comprising:

a first amphiphilic part corresponding to one of formulae (I) or (II):

wherein i is an integer ranging from 1 to 20 and j is an integer ranging from 3 to 30, and a second part to which the first part of the compound is chemically bonded, the second part capable of complexing a chemical entity, wherein the compound has the property of being soluble in water below a critical temperature T$_c$ and insoluble in water above the temperature T$_c$ the property being thermally reversible.

2. The compound according to claim 1, wherein the second part comprises an amino acid, a peptide, an oligopeptide, a polypeptide, an oligomer, or a polymer comprising one or more complexing groups of amine, amide, or acid.

3. The compound according to claim 2, wherein the second part comprises a single amino acid.

4. The compound according to claim 3, wherein the amino acid is lysine.

5. The compound according to claim 4, wherein the second part of the compound corresponds to formula (III):

wherein R¹ is a hydrocarbonaceous group and R² is a hydroxyl group, an alkoxy group, or a nitrogenous group which may or may not be substituted.

6. The compound according to claim 5, wherein R¹ is a methyl group and R² is a hydroxyl group or a methoxy group.

7. The compound according to claim 1, wherein the critical temperature $T_c$ is 20 to 90° C. at a concentration by weight of 0.1 to 25% in aqueous solution.

8. A compound corresponding to formula (IV):

(IV)

wherein i is equal to 12, j is equal to 4, R¹ is $CH_3$, and R² is $OCH_3$.

9. A compound corresponding to formula (V):

(V)

wherein i is equal to 12, j is equal to 5, R¹ is $CH_3$, and R² is $OCH_3$ or OH.

10. The compound according to claim 8, wherein the compound has a critical temperature $T_c$ of 55 to 75° C. at a concentration by weight of 0.5 to 25% in aqueous solution.

11. The compound according to claim 9, wherein the compound has a critical temperature $T_c$ of 30 to 70° C. at a concentration by weight of 0.1 to 25% in aqueous solution.

12. A process for the preparation of a heat-sensitive compound having the property of being soluble in water below a critical temperature $T_c$ and insoluble in water above the temperature $T_c$ the property being thermally reversible, the process comprising:

reacting a carboxylic derivative corresponding to one of formulae (VI) or (VIII):

(VI)

(VIII)

wherein i is an integer ranging from 1 to 20, j is an integer ranging from 3 to 10, and R³ is Cl, OH, or an alkoxy group, with a primary or secondary amine or polyamine comprising a group capable of complexing a chemical entity.

13. A process for the preparation of a compound of formula (IV):

(IV)

wherein i is an integer ranging from 1 to 20, j is an integer ranging from 3 to 30, R¹ is a hydrocarbonaceous group, and R² is a hydroxyl group, an alkoxy group, or a nitrogenous group which may or may not be substituted, the process comprising:

reacting a carboxylic derivative of formula (VI):

(VI)

wherein i and j are as defined above in formula (IV) and R³ is Cl, OH, or an alkoxy group, with a lysine derivative of formula (VII):

(VII)

wherein R¹ and R² are as defined above for formula (IV).

14. The process according to claim 13, wherein the hydroxyl group of the carboxylic derivative of formula (VI) is protected and the carboxyl group of the derivative is activated before reacting it with the lysine derivative of formula (VII).

15. The process according to claim 14, wherein the hydroxyl group is protected with tetrahydropyran and the carboxyl group is activated with N-hydroxysuccinimide.

16. The process according to claim 14, further comprising a step of deprotecting the hydroxyl group of the derivative of formula (VI) after reaction of the derivative of formula (VI) with the lysine derivative of formula (VII).

17. A process for the preparation of a compound of formula (V):

(V)

wherein i is an integer ranging from 1 to 20, j is an integer ranging from 3 to 30, R¹ is a hydrocarbonaceous group, and R² is a hydroxyl group, an alkoxy group, or a nitrogenous group which may or may not be substituted, the process comprising:

reacting a carboxylic derivative of formula (VIII):

(VIII)

wherein i and j are as defined above for formula (V) and R³ is Cl, OH, or an alkoxy group,
with a lysine derivative of formula (VII):

(VII)

wherein $R^1$ and $R^2$ are as defined above for formula (V).

18. A process for the extraction of at least one chemical entity present in an aqueous solution, comprising the steps of:
   a) adding a heat-sensitive compound according to claim 1 to the aqueous solution at a temperature lower than the critical temperature $T_c$ of the compound to form a reaction medium,
   b) bringing the reaction medium to a temperature greater than the critical temperature $T_c$ of the compound in order to separate the reaction medium into two phases, the two phases being a concentrated phase enriched in the chemical entity to be extracted, the concentrated phase having a density greater than that of water and which sediments, and a supernatant dilute aqueous phase depleted in the chemical entity to be extracted, and
   c) separating the phase concentrated in the chemical entity from the reaction medium.

19. A process for the extraction of at least one chemical entity present in an aqueous solution, comprising the steps of:
   a) adding a heat-sensitive compound according to claim 1 and a water-immiscible organic phase to the aqueous solution at a temperature lower than the critical temperature $T_c$ of the compound to form a reaction medium,
   b) bringing the reaction medium to a temperature greater than the critical temperature $T_c$ in order to transfer the heat-sensitive compound and the chemical entity to be extracted into the organic phase, and
   c) separating the organic phase comprising the chemical entity from the reaction medium.

20. The process according to claim 18, wherein the amount of heat-sensitive compound added in step a) is such that the concentration by weight of heat-sensitive compound in the aqueous solution is from 0.1 to 25%.

21. The process according to claim 18, wherein the chemical entity to be extracted is uranium present in the form of uranyl ion in the aqueous solution.

22. The process according to claim 21, wherein the heat sensitive compound corresponds to formula (IV):

(IV)

wherein i is equal to 12, j is equal to 4, $R^1$ is $CH_3$, and $R^2$ is $OCH_3$.

23. The process according to claim 19, wherein the amount of heat-sensitive compound added in step a) is such that the concentration by weight of heat-sensitive compound in the aqueous solution is from 0.1 to 25%.

24. The process according to claim 19, wherein the chemical entity to be extracted is uranium present in the form of uranyl ion in the aqueous solution.

25. The process according to claim 24, wherein the heat-sensitive compound corresponds to formula (IV):

(IV)

wherein i is equal to 12, j is equal to 4, $R^1$ is $CH_3$, and $R^2$ is $OCH_3$.

* * * * *